United States Patent [19]

Schmidt

[11] Patent Number: 4,524,216

[45] Date of Patent: Jun. 18, 1985

[54] METHOD OF PREPARING P-ORSELLINIC ACID ESTERS

[75] Inventor: Hans-Georg Schmidt, Niederkassel, Fed. Rep. of Germany

[73] Assignee: Dynamit Nobel AG, Cologne, Fed. Rep. of Germany

[21] Appl. No.: 532,199

[22] Filed: Sep. 14, 1983

[30] Foreign Application Priority Data

Sep. 22, 1982 [DE] Fed. Rep. of Germany ....... 3235019

[51] Int. Cl.³ .............................................. C07C 69/88
[52] U.S. Cl. ....................................................... 560/70
[58] Field of Search ......................................... 560/70

[56] References Cited

FOREIGN PATENT DOCUMENTS 0074497  3/1983  European Pat. Off. .............. 560/70

*Primary Examiner*—Paul J. Killos
*Attorney, Agent, or Firm*—Felfe & Lynch

[57] ABSTRACT

Resorcinols of the structure of p-orsellinic acid ester are obtained from pyrones of the formula

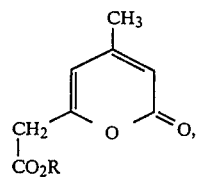

by the action of no more than catalytic amounts of bases.

14 Claims, No Drawings

METHOD OF PREPARING P-ORSELLINIC ACID ESTERS

BACKGROUND OF THE INVENTION

The invention relates to a method of preparing resorcinols of the structure of p-orsellinic acid alkyl esters of the formula

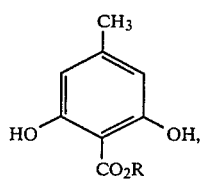

wherein R represents alkyl groups of 1 to 6 carbon atoms, by the action of strong bases on pyrones of the formula

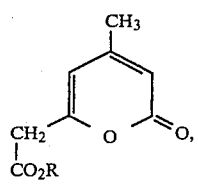

wherein R has the meaning given above.

The transposition of the alpha-pyrones of formula II with bases to form resorcinols of formula I is known from DE-AS 12 12 533. That disclosure, however, expressly describes the use of at least one mole of a strong base per mole of pyrone. When working up the product, it is then necessary to neutralize the base with correspondingly large amounts of acids, since otherwise the base forms salts with the hydroxyl groups of resorcinol, and these salts prevent the separation and recovery of the resorcinol.

The problem therefore was to avoid the use of these large amounts of bases and acids as well as the working up of the salts that are formed.

BRIEF DESCRIPTION OF THE INVENTION

It has been found that the pyrones of formula II where R is an alkyl group of 1 to 6 carbon atoms can be reacted in the presence of only catalytic amounts of a base to form the resorcinols of formula I.

Bases that are suitable are alkali or alkaline earth hydroxides, alcoholates, amides, and hydrides, or alkali carbonates, such as for example sodium hydroxide, sodium methylate, sodium amide, lithium hydride or sodium carbonate. The bases are used in less than stochiometric amounts of 0.01 to 95 mol-%, especially 0.01 to 80 mol-%, preferably 0.01 to 30 mol-%, with respect to formula II.

The reaction can be performed in the presence or absence of a solvent. The following, for example, are used as solvents: alcohols of 1 to 6 carbon atoms such as methanol or ethanol, for example, dimethylformamide, toluene, and tetrahydrofuran.

The reaction temperatures are between 20° and 180° C. Standard pressure is preferred.

The alkyl group R is preferably a methyl or ethyl group.

The starting material is easily accessible, for example in accordance with the information given in DE-AS No. 12 12 533.

A preferred embodiment of the transposition is to add to a solution of the pyrone of formula II in one of the above solvents catalytic amounts of base, and boiling, with refluxing if desired. The work-up is performed by precipitation with water, followed if desired by acidification with mineral acids such as HCl or $H_2SO_4$, or low organic acids, such as acetic acid, for example. The raw product can be purified by distillation or recrystallization.

The method of the invention has considerable advantages over the state of the art. The amount of the adjuvant base is considerably reduced. The neutralization, the amount of acid involved and the production of salt is low. Furthermore, higher yields are achieved by the use of small amounts of base. In the use of 100 mol-% of base, the yield of formula I up to the complete reaction of II is 84%. Reducing the amount of base to 10 mol-% increases the yield of I to 90% (See Example 1).

p-Orsellinic acid ester is an intermediate for the preparation of, for example, additives for rocket fuels, stabilizers for plastics, coupling components for diazotype printing, and agents for the protection of plants.

p-Orsellinic acid methyl ester for example can be reacted into the antibioticum tetracycline (D. H. R. Barton et. al.: J. Chem. Soc. (C) 1971, pages 2215 ff). p-Orsellinic acid formed from the ester can be used for the production of thermally developable diazo duplicating materials (Japanese patent publication 74/1562, filed as Ja 72379/69 on 12.09.1969).

EXAMPLES

Example 1

20 g (0.11 mol) of 4-methyl-alpha-pyronyl-6-acetic acid methyl ester and 10 ml of methanol are mixed with 1.19 g of a 25 wt-% sodium methylate solution in methanol (=0.0055 mol=5 mol-%), and this mixture is refluxed for 19.5 hours. After cooling, the reaction mixture is acidified with a 10% solution (by weight) of HCl, and the crystals that precipitate are suction filtered and distilled after drying. 18.0 g (0.99 mol) of p-orsellinic acid methyl ester is obtained (yield 90%).

Examples 2 to 5 and Prior-Art Example A

The reaction temperature and the amount of catalyst were varied in the procedure of Example 1 as follows:

| Example No. | $NaOCH_2$ mol % with respect to II | Temperature °C. | Reaction Time hrs. | Yield % |
|---|---|---|---|---|
| A | 100 | 20 | 0.5 | 84 |
| 2 | 75 | 20 | 0.5 | 85 |
| 3 | 25 | 40 | 5.0 | 85 |
| 4 | 10 | 68 | 4.5 | 90 |
| 5 | 1 | 68 | 30 | 89 |

Example 6

20 g of 4-methyl-alpha-pyronyl-6-acetic acid methyl ester and 20 ml of toluene are mixed with 0.6 g of sodium methylate and this mixture is refluxed for 23 hours. Then it is acidified with 2N HCl, the organic phase is separated, and the toluene is distilled out. The residue is recrystallized from methanol. 17 g of p-orsellinic acid methyl ester is obtained.

Example 7

A mixture of 20 g of 4-methyl-alpha-pyronyl-6-acetic acid ethyl-ester and 20 ml of ethanol is refluxed with 2 g of sodium carbonate for 24 hours. Then the mixture is acidified with 2N $H_2SO_4$ and the precipitated crystals are removed on a suction filter. After drying and recrystallization from methanol, 16 g of p-orsellinic acid ethyl ester is obtained.

Example 8

20 g of 4-methyl-alpha-pyronyl-6-acetic acid methyl ester and 10 ml of methanol are refluxed for 30 hours with 0.238 g of a 25 wt-% sodium methylate solution in methanol. Upon the addition of 30 ml of water the raw product precipitates. After recrystallization from methanol 17.8 of p-orsellinic acid methyl ester is obtained.

It will be understood that the specification and examples are illustrative but not limitative of the present invention and that other embodiments within the spirit and scope of the invention will suggest themselves to those skilled in the art.

Example 9

Example 1 was repeated with the equivalent amount of calcium methylate resulting in corresponding yields of the product noted in example 1.

I claim:

1. Method of preparing resorcinols of the formula

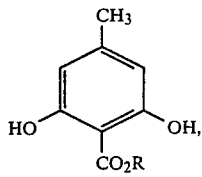

I wherein R represents alkyl groups of 1 to 6 carbon atoms, by the action of strong bases on pyrones of the formula

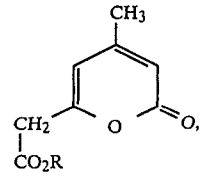

II wherein R has the above meaning, characterized in that the base is used in catalytic amounts.

2. The method of claim 1, wherein the base is selected from the group consisting of alkali alcoholates, alkaline earth alcoholates, alkali hydroxides, alkaline earth hydroxides and/or alkali carbonates.

3. The method of claim 2 wherin the reaction is carried out at temperatures of 20° to 180° C.

4. The method of claim 1, wherein the reaction is carried out in a solvent.

5. The method of claim 2 wherein the reaction is carried out in a solvent.

6. The method of claim 3 wherein the reaction is carried out in a solvent.

7. The method of claim 2 wherein R is methyl.

8. The method of claim 7 wherein the base is sodium methylate.

9. The method of claim 4 wherein the solvent is an alcohol of 1 to 6 carbon atoms, dimethylformamide, toluene and tetrahydrofuran.

10. The method of claim 7 wherein the base is sodium carbonate.

11. The method of claim 1 wherein the base is present in 0.01 to 0.5 mol percent with respect to the pyrone.

12. The method of claim 1 wherein the base is present in 0.01 to 80 mol percent with respect to the pyrone.

13. The method of claim 1 wherein the base is present in 0.01 to 30 mol percent with respect to the pyrone.

14. The method of claim 2 wherein the reaction is carried our at temperatures of 20° to 100° C.

* * * * *